(12) United States Patent
Eda et al.

(10) Patent No.: US 7,142,902 B2
(45) Date of Patent: *Nov. 28, 2006

(54) DEVICE FOR MEASURING STRATEGY ACQUISITION AND METHOD FOR MEASURING STRATEGY ACQUISITION

(75) Inventors: Hideo Eda, Tokyo (JP); Yasufumi Kuroda, Tokyo (JP)

(73) Assignee: National Institute of Information and Communications Technology, Tokyo (JP)

( * ) Notice: Subject to any disclaimer, the term of this patent is extended or adjusted under 35 U.S.C. 154(b) by 319 days.

This patent is subject to a terminal disclaimer.

(21) Appl. No.: 10/799,501

(22) Filed: Mar. 11, 2004

(65) Prior Publication Data

US 2004/0236197 A1 Nov. 25, 2004

(30) Foreign Application Priority Data

Mar. 14, 2003 (JP) ............................ P2003-069919
Jan. 14, 2004 (JP) ............................ P2004-007366

(51) Int. Cl.
*A61B 5/00* (2006.01)

(52) U.S. Cl. ...................... 600/340; 600/323; 600/300

(58) Field of Classification Search ................ 600/309, 600/310, 322, 323, 340, 382, 383
See application file for complete search history.

(56) References Cited

U.S. PATENT DOCUMENTS

2004/0100618 A1* 5/2004 Barker ........................ 351/206

OTHER PUBLICATIONS

Hoshi et al., Near-Infrared Optical Detection of Sequential Brain Activation in the Prefrontal Cortex during Mental Tasks (May 1997), NeuroImage, vol. 5, p. 292-297.*

Baird et al., Frontal Lobe Activation during Object Permanence: Data from Near-Infrared Spectroscopy (Aug. 2002), NeuroImage, vol. 16, p. 1120-1126.*

"Preliminary Synthesis of the First High Level Forum on Learning Sciences and Brain Research: Brain Mechanisms and Early Learning", prepared by the OECD-CERI Secretariat with particular assistance from Mr. Bruno Levy, Sackler Institute, New York, New York, Jun. 16-17, 2000, pp. 1-38.

* cited by examiner

*Primary Examiner*—Eric Winakur
*Assistant Examiner*—Etsub Berhanu

(57) ABSTRACT

The present claimed invention intends to provide a simple and superior means that is possible to express a tendency or a characteristic of a learner as scientific data by making use of a fact that a blood amount or/and a blood component amount in a predetermined region of brains causes a characteristic change when a learner acquires strategy to solve a work during a process of solving the work and that is effective for developing a new educational method from the scientific data. In case a subject conducts a predetermined work, a blood amount or/and a blood component amount in a predetermined measuring region of brains of the subject is measured chronologically by the use of a near-infrared spectroscopy, time change data as data showing time change of the blood amount or/and the blood component amount is produced and a state of strategy acquisition to solve the work for the subject is determined based on the time change data.

13 Claims, 11 Drawing Sheets

DEVICE FOR MEASURING STRATEGY ACQUISITION AND METHOD FOR MEASURING STRATEGY ACQUISITION

BACKGROUND OF THE INVENTION

1. Field of the Invention

This invention relates to a device for measuring strategy acquisition and a method for measuring strategy acquisition to a target work for a subject by making use of a change of brain activities of the subject.

2. Description of the Related Art

Conventionally a variety of methods have been presented to enhance an educative effect and recently a new educational method is also being developed with employing personal computers. (Refer to Japan Patent Publication No. HEI8-227266.)

It is essential for educators to grasp ability or a characteristic of a learner in order to provide the learner with an appropriate education.

For example, some works in mathematics and arithmetic, especially geometrical works can be answered smoothly by acquiring "strategy" to solve a relevant work such as finding a definite law or regularity and making use of it. As a concrete example of the work represented is a work such as a given graphical form is judged to be congruent with a predetermined graphical form or not is conducted at multiple times wherein once a learner acquires "strategy" on which part of the graphical form the learner should focus attention in order to compare the graphical forms so as to judge the given graphical form to be congruent with the predetermined graphical form or not, the learner can later solve the work by making use of the "strategy". In addition to this, the work includes the one if where to draw an additional line is come to mind for a learner and later the learner can reach a solution by making a calculation from a known formula, and in this case utilization of the appropriate additional line can be "strategy" for solving a work.

In case that a learner solves the above-mentioned work, it is conceived that there are two processes, one of which is a process until the learner acquires "strategy" and the other of which is a process after the learner acquires the "strategy". Since there was conventionally neither a device nor a method to separate two processes, a problem solving ability of the learner was judged by whether the work was solved or not to the last and if solved, how long it took the learner to solve the work.

As mentioned above, however, with this conventional judgment it was impossible to judge whether the learner who could not solve the work "could not acquire strategy" or "could acquire strategy and made a mistake in a later process of calculation or the like". In addition, for a learner who could solve the work it was impossible to grasp a tendency (strong and weak points) in solving the work such that whether the learner took time until he or she acquired strategy or after he or she acquired strategy. As a result of this, it is not possible to provide a learner with an appropriate educational guidance. These points at issue are not limited to the works in mathematics or arithmetic.

In the mean time, a variety of devices that can measure brain activities without constraining a movement of a subject in a non-invasive manner have been developed apart from an electroencephalograph, a CT scanner or an MRI system and a progress in a study of brain science has been amazing.

The present claimed invention intends to obtain an objective scientific data of a learner during an intellectual process that had not been obtained before by applying the brain science to an educational field and to utilize the scientific data in a guidance of an educational field. More specifically, the present claimed inventor has found that a blood amount or/and a blood component amount in a predetermined region of brains causes a characteristic change when a learner acquires strategy to solve a work during a process of solving the work and by making use of the findings a simple and superior means that is possible to express a tendency or a characteristic of a learner as scientific data and that is effective for developing a new educational method from the scientific data is provided.

BRIEF SUMMARY OF THE INVENTION

A device for measuring strategy acquisition in accordance with the present claimed invention comprises a measuring portion that measures a blood amount or/and a blood component amount in a predetermined measuring region of brains of a subject, a time change data producing portion that obtains the blood amount or/and the blood component amount measured by the above-mentioned measuring portion chronologically and produces time change data as data showing time change of the blood amount or/and the blood component amount and an output portion that outputs the time change data produced by the time change data producing portion in case the subject conducts a predetermined work, so that timing when the subject acquires strategy to solve the work can be detectable.

"Strategy acquisition" here is to happen to know an appropriate answer or an appropriate way to solve a work and also includes to find a definite law or regularity or to find a clue to solve a work.

In accordance with the arrangement, it is possible to know which timing the subject acquires strategy to the work or to know whether the subject can acquire strategy to the work or not as objective scientific data from the time change of the blood amount or/and the blood component amount in the predetermined measuring portion of the brain. More specifically, it is possible to judge a problem solving ability of the subject that used to be judged only from a total time taken to solve the problem divided into a process before acquiring strategy and a process after strategy is acquired. As a result, a learning instructor can get a tendency or a characteristic of a learner, thereby to provide a big possibility in developing a new educational method appropriate for each learner or in designing a curriculum of education objectively.

Further, since the blood amount and/or the blood component amount is measured, it is possible to conduct measurement in a non-invasive manner without constraining a movement of the subject and with a simple arrangement, for example, by making use of a near-infrared spectroscopy. In addition, since the near-infrared spectroscopy is superior in time resolution, it is possible to obtain data in detail showing a state of strategy acquisition.

An output portion may have an arrangement to graph out or numerically express time change or to provide an appropriate process so as to express timing of strategy acquisition numerically. As an output portion with a relatively simple arrangement and easy to understand for an experimenter represented is an output portion that outputs a waveform of the time change data during conducting the above-mentioned predetermined work.

In addition, as the measuring portion represented is a measuring portion that measures an amount of oxyHb (oxygenated hemoglobin) and an amount of deoxyHb (deoxygenated hemoglobin) in blood. This is because there is a distinguished relationship between time change of the oxyHb amount and the deoxyHb amount and strategy acquisition. In case that the output portion outputs the waveform of the time change data as represented in claim 2, a waveform of the time change data in accordance with the oxyHb amount and the deoxyHb amount may be output.

In addition, it is preferable that the output portion further outputs timing when the subject completes the work in a manner comparable with the time change data. This is because that a relationship between completion of work and the time change data of the blood amount or/and the blood component amount can be shown specifically. In a mode wherein multiple works to be solved by the same strategy are continuously solved within a predetermined duration "completion of work" here shows completion of each of the multiple works respectively.

As a preferable position set as the predetermined measuring region represented is an area corresponding to a higher brain function portion. More concretely, it is preferable that the predetermined measuring region is set at a frontal lobe. In accordance with this arrangement, measurement can be conducted with ease and a burden to a subject can be minimized.

As mentioned above; as a preferable concrete arrangement of the measuring portion represented is a measuring portion that measures the blood amount or/and the blood component amount by making use of a near-infrared spectroscopy. In this case, the measuring portion is not necessarily be multi-channel and a type of one channel produces sufficient effects of the present claimed invention.

In order to obtain accurate data by restraining a movement of a head portion of the subject who is solving the work during measurement it is preferable that a fixing means to fix the head portion of the subject is further provided.

In order to measure timing of strategy acquisition more accurately, it is preferable that the measuring portion can calculate a blood amount or/and blood component amount that is baseline-corrected corresponding to the work conducted by the subject and the time change data producing portion is made to obtain the baseline-corrected blood amount or/and blood component amount chronologically and produce the time change data. "Corresponding to the work" means that corresponding to difference of contend of works or corresponding to an embodiment.

In solving a work that requires strategy, a considerable big psychological load is applied to the subject compared with a normal state. More specifically, a value of a blood amount or/and a blood component amount resulting from a change of a psychological state for the subject might have en effect on time change data in addition to a brain noise. Furthermore, a degree of the effect varies depending on a content of the work or an embodiment. As a result, in accordance with the arrangement, the effect on a measured value given by the psychological load can be eliminated, thereby to obtain highly reliable data.

In case that the measuring portion calculates a measured value of the blood amount or/and the blood component amount based on a predetermined parameter data that is correlative to the blood amount or/and the blood component amount, as a concrete arrangement of the measuring portion represented is that further comprises a parameter data correct portion that baseline-corrects the above-described parameter corresponding to the work and a computing portion that calculates the blood amount or/and the blood component amount by the use of the parameter data corrected by the parameter data correct portion.

In this case, it is preferable that the parameter data correct portion is to correct the parameter data by subtracting baseline data expressing a baseline from the parameter data and the baseline data is expressed by a function that varies corresponding to a content of the work.

In brief, in case the subject conducts a predetermined work, a method for measuring strategy acquisition may be such that a blood amount or/and a blood component amount in a predetermined measuring region of brains of a subject is measured chronologically by the use of a near-infrared spectroscopy, time change data as data showing time change of the blood amount or/and the blood component amount is produced and a state of strategy acquisition to solve the work for the subject is determined based on the time change data.

In accordance with the present claimed invention, it is possible to know which timing the subject acquires strategy to the work or to know whether the subject can acquire strategy to the work or not as objective scientific data from the time change of the blood amount or/and the blood component amount in the predetermined measuring portion of the brain. More specifically, it is possible to judge a problem solving ability of the subject that used to be judged only from a total time taken to solve the problem divided into a process before acquiring strategy and a process after strategy is acquired. As a result, a learning instructor can get a tendency or a characteristic of a learner, thereby to provide a big possibility in developing a new educational method appropriate for each learner or in designing a curriculum of education objectively.

DETAILED DESCRIPTION OF THE INVENTION

A preferred embodiment of the present claimed invention will be described in detail with reference to the accompanying drawings.

First Embodiment

Figure 1:
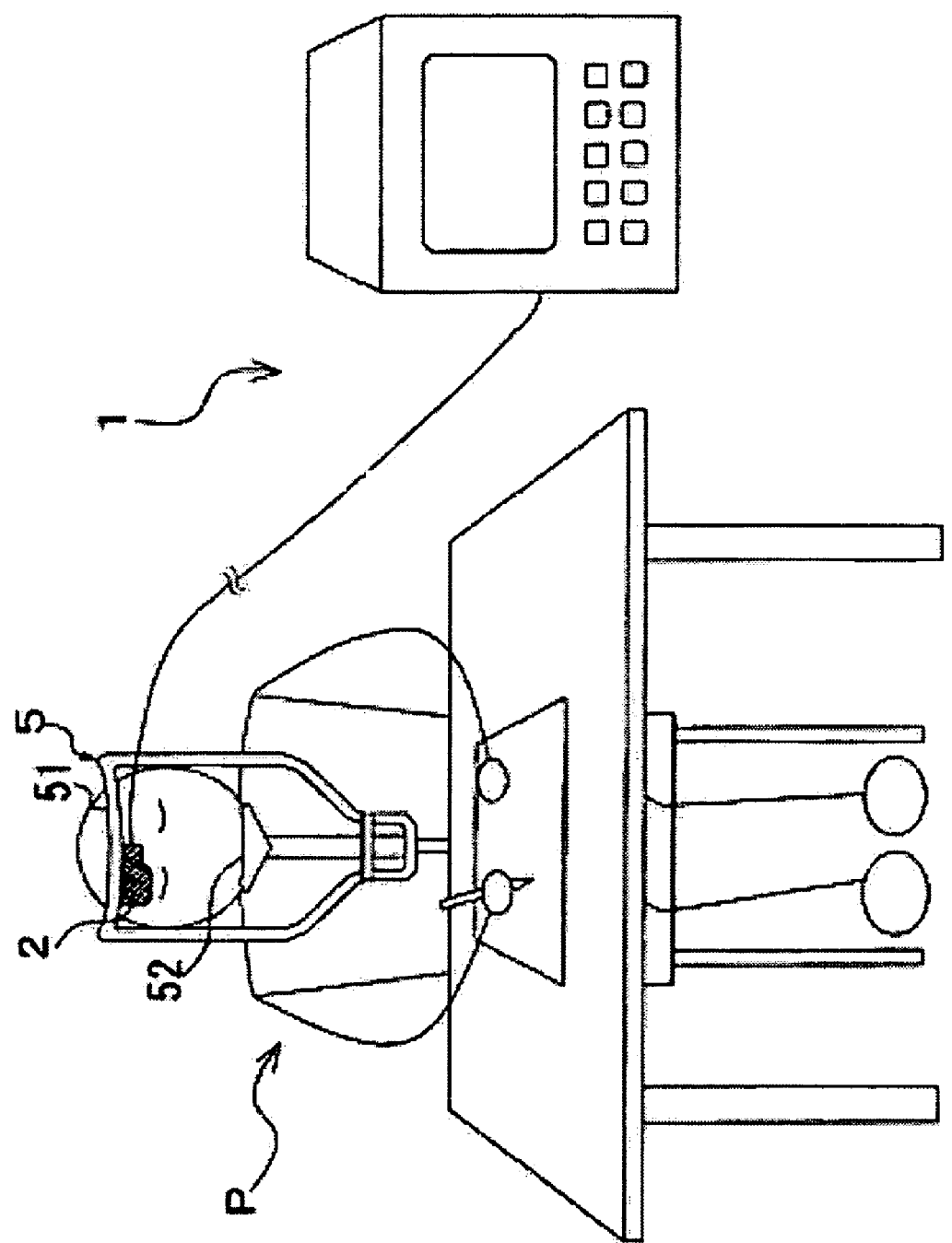
FIG. 1 is a schematic view showing a device for measuring strategy acquisition in accordance with one embodiment of the present claimed invention.
Figure 3:
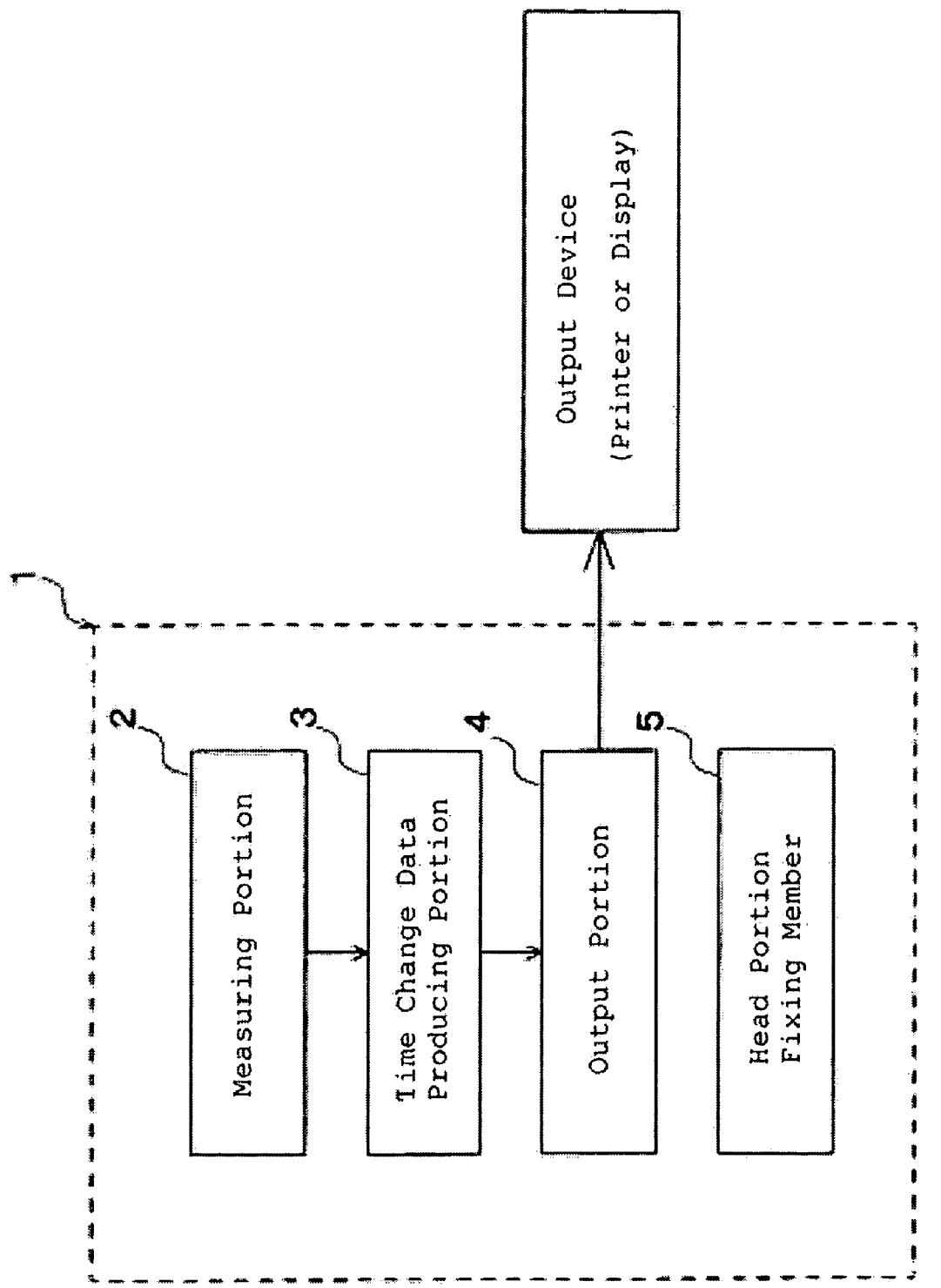
FIG. 3 is a whole functional structural view of the device for measuring strategy acquisition in accordance with the embodiment.

A device for measuring strategy acquisition 1 in accordance with this embodiment comprises, as shown in FIG. 1 and FIG. 3, a measuring portion 2 that measures a blood component amount in a predetermined measuring region S of brains of a subject P, a time change data producing portion 3 that obtains the blood component amount measured in the above-mentioned measuring portion 2 chronologically and produces time change data as data showing time change of the blood component amount, in case the subject P conducts a predetermined work, an output portion 4 that outputs the time change data produced by the time change data producing portion 3 so that timing of strategy acquisition for the subject P to perform the work can be detectable and a head portion fixing member 5 as a fixing means to fix a head portion of the subject P.

Figure 4:
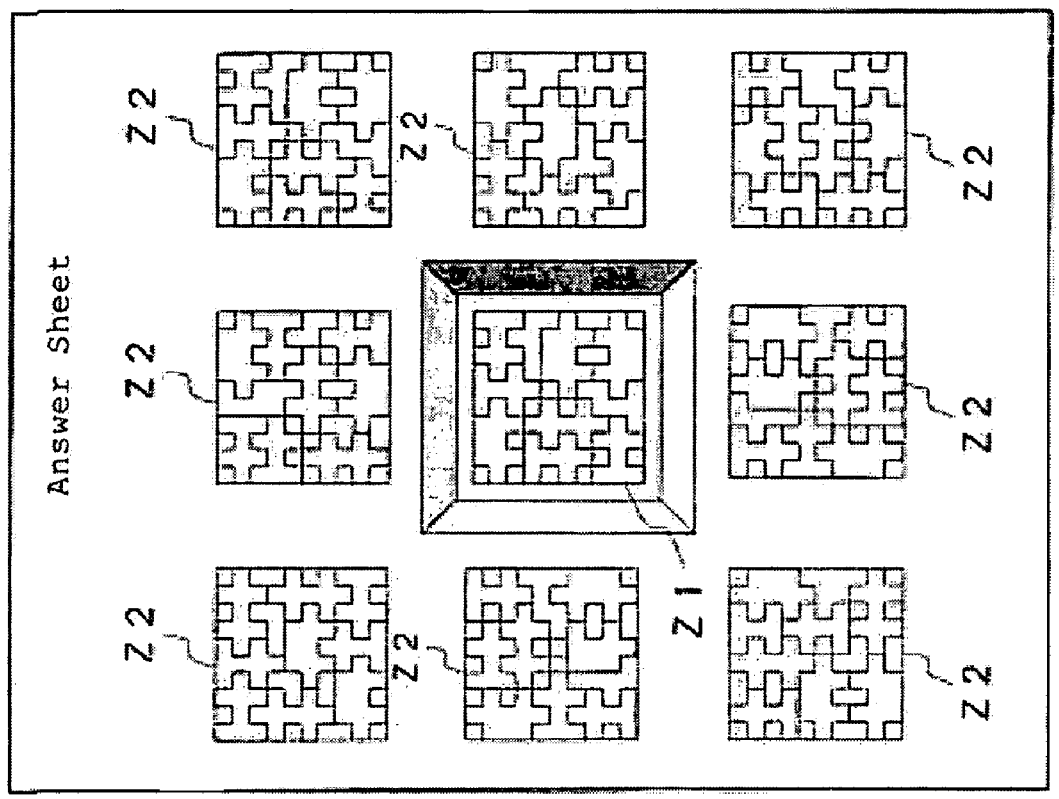
FIG. 4 is a view showing a content of a work in accordance with the embodiment.
Figure 4:
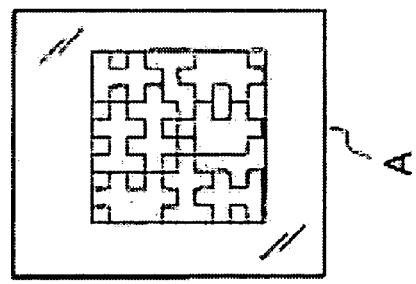

First, the predetermined work to be conducted by the subject P will be explained. In this embodiment, the work is to answer whether a predetermined two-dimensional designated graphic form Z1 is congruent with a work graphic form Z2 or not as shown in FIG. 4. A graphic form that is parallel to, line-symmetric to or turned around the designated graphic form Z1 is considered to be congruent. The designated graphic form Z1 shown in FIG. 4 is arranged at a center of a work sheet and a pattern is drawn in a square (for example, 3.2 cm×3.2 cm). Multiple (eight in this embodiment) work graphic forms Z2 are arranged around the designated graphic form Z1 in a shape of a grid and patterns are drawn inside each square whose size is the same as that of the square of the designated graphic form Z1. In the work of this embodiment, a transparent auxiliary sheet A on which a graphic form congruent with the designated graphic form Z1 is printed is prepared and whether each of the work graphic forms Z2 is congruent with the designated graphic form Z1 or not is judged by making use of the auxiliary sheet A.

During this work, "strategy is acquired" to perform the work is not just to compare the designated graphic form Z1 with a work graphic form Z2 aimlessly but to find a key to be checked in order to judge whether each of these graphic forms is congruent or not and to judge it by making use of the auxiliary sheet A or to judge it in mind alone.

Next, a concrete arrangement of each portion of the device 1 will be described. The measuring portion 2 makes use of an NIRS (a near-infrared spectroscopy) wherein near-infrared light of multiple different wave lengths (three wave lengths in this embodiment) radiated from semiconductor lasers or the like are irradiated on the predetermined measuring region S and each of the near-infrared light reflecting off inside the brains is received by a photo acceptance element and calculates an oxyHb amount and a deoxyHb amount in blood or tissue by measuring absorbance (absorption of light) of each wave length of near-infrared light obtained based on the light intensity of irradiated light and reflected light directly.

Figure 2:
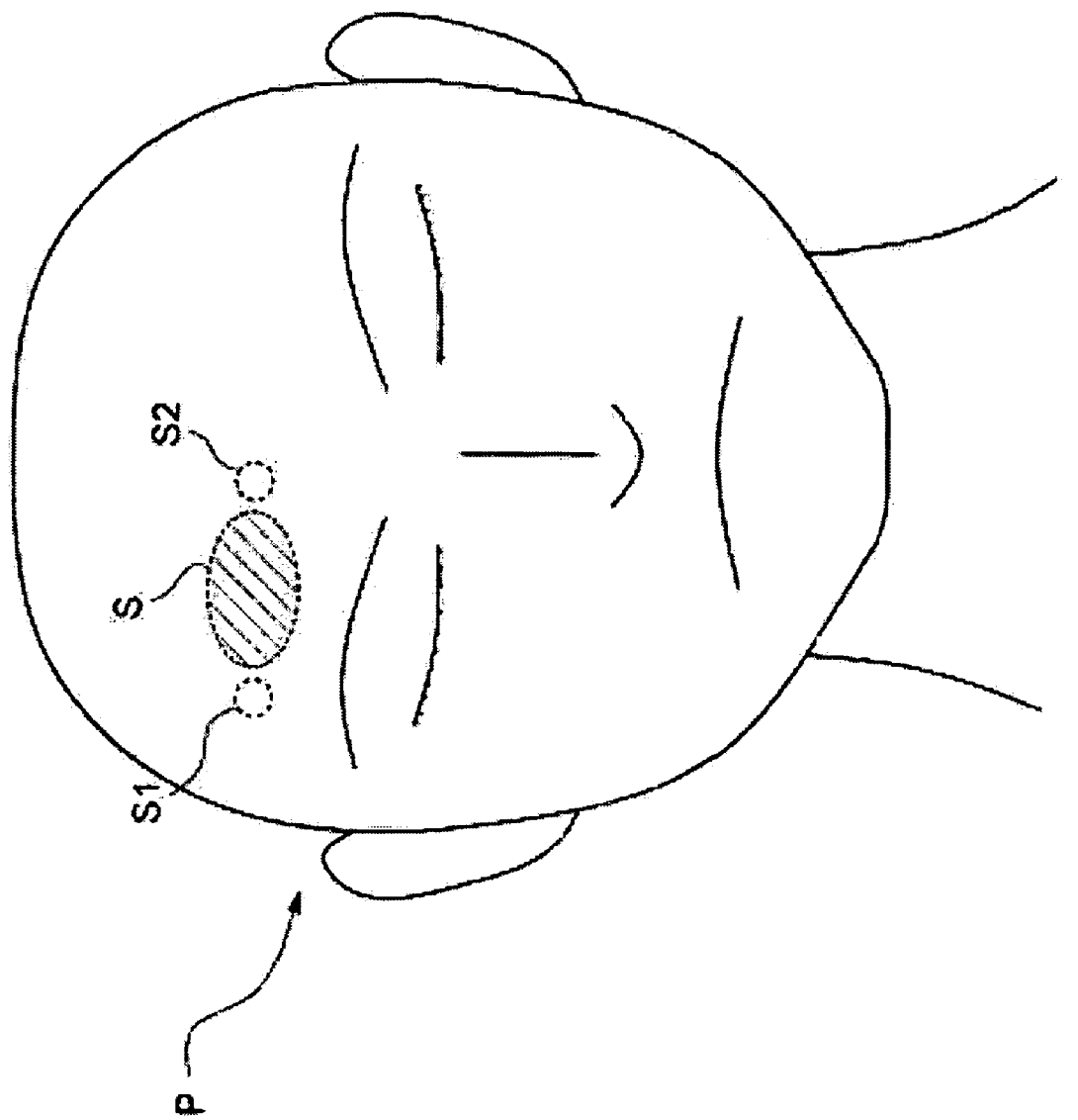
FIG. 2 is an explanatory view of a part showing a predetermined measuring region in accordance with the embodiment.

In this embodiment, the measuring portion 2 is a type of one channel, namely, having a pair of a light incident portion and a light receiving portion wherein each of the light incident portion and the light receiving portion is mounted on a predetermined area S1 and a predetermined area S2 respectively of a forehead of the subject P, as shown in FIG. 2, and measures the oxyHb amount and the deoxyHb amount in the predetermined measuring region S between the predetermined areas S1 and S2. The predetermined measuring region S is a higher brain function portion and set at, for example, the frontal lobe of the subject P in this embodiment. In order to determine the predetermined measuring region S, first a brain structural image of the subject P is obtained by the use of a device such as an MRI for measuring a brain structure and then the predetermined measuring region S is determined based on the above-obtained brain structural image. More concretely, the predetermined measuring region S locates in a region where the brains protrude most in a right prefrontal area. Substantial reasons for this are the right prefrontal area is a region other than a region dominating language, the right prefrontal area is considered to be related to a graphics processing according to an antecedent study and the right prefrontal area is easy to measure because the area has no hair.

The time change data producing portion 3 chronologically obtains the oxyHb amount and the deoxyHb amount measured by the measuring portion 2 during a process while the subject P conducts the above work by sampling them at predetermined intervals and stores each amount in a predetermined memory portion so as to produce time change data as data showing time change of the oxyHb amount and the deoxyHb amount and time change of a total hemoglobin amount calculated by the oxyHb amount and the deoxyHb amount. In this embodiment the data are processed in a digital manner by the use of a CPU, however, it is a matter of course that the data may be processed in an analog manner so as to produce time change data.

The output portion 4 outputs a waveform of time change data during the process while the subject P conducts the work to a display or a printer. Further, as shown by x in FIG. 5, the output portion 4 outputs timing (timing of completing a work) that the subject P completes a single work and the waveform simultaneously with a chronological order aligned so as to be compared. In this embodiment, the timing of completing the work is measured, for example, by making use of a picture taken by a video camera or the like.

The head portion fixing member 5 comprises, for example as shown in FIG. 1, a forehead supporting portion 51 that supports an upper portion of a forehead of the subject P, a chin supporting portion 52 that supports a chin of the subject P and a fixing portion, not shown in drawings, that fixes the forehead supporting portion 51 and the chin supporting portion 51 to a desk on which the subject P is to be seated or a floor in an immobilized state.

Figure 5:
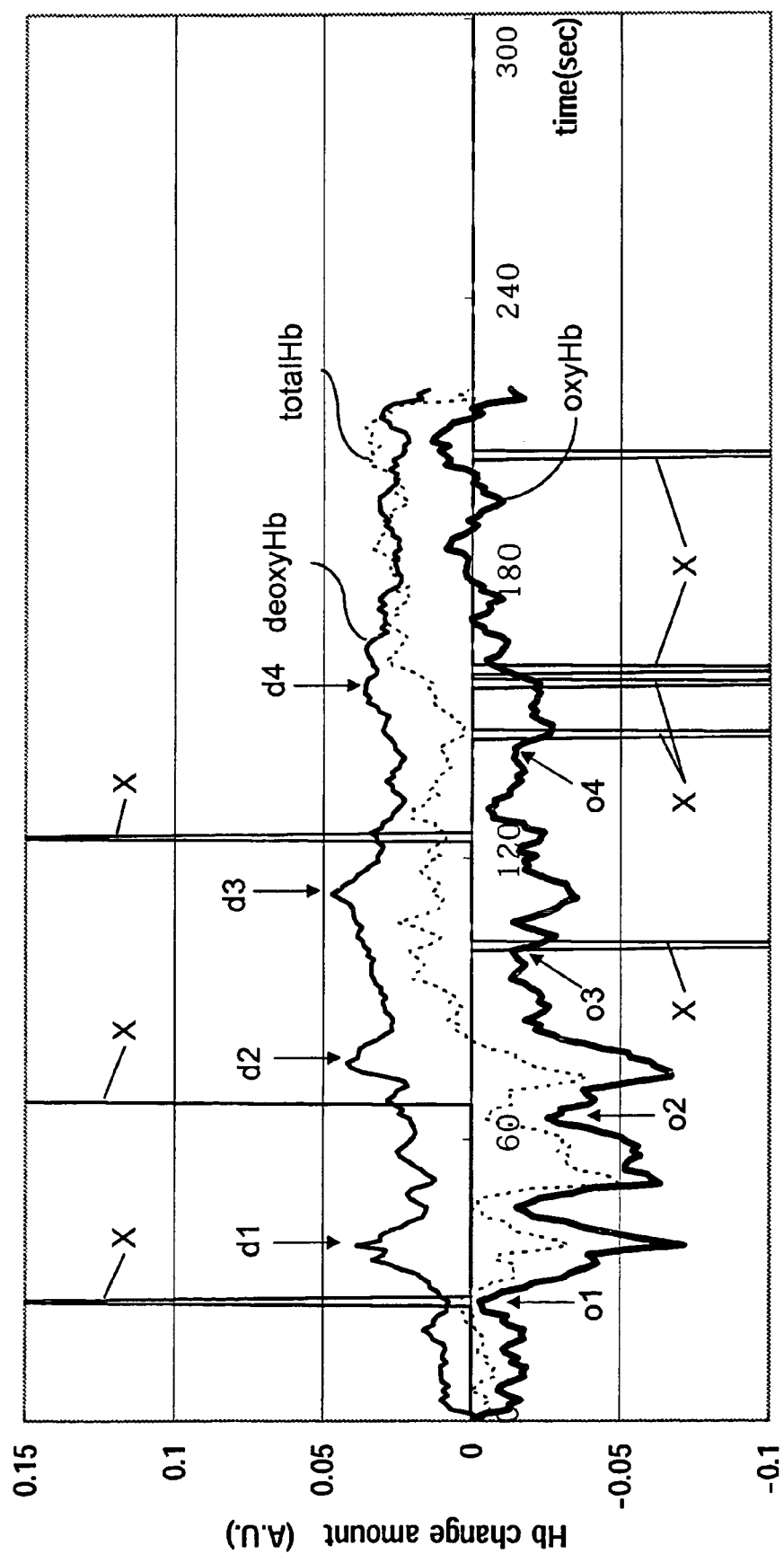
FIG. 5 is a waveform chart showing a waveform of time change data during a process of performing a work in accordance with the embodiment.

Next, an example of a result when the subject P actually conducts the above-mentioned work by the use of the device for measuring strategy acquisition 1 in accordance with the embodiment will be shown with reference to FIG. 5. In FIG. 5, each upward facing peak is timing when the subject P determines the work as congruent and fills in, for example, ○ and each downward facing peak is timing when the subject P determines the work as not congruent and fills in, for example, x out of the timing of completion of works shown by x.

As is clear from FIG. 5, a total time to perform the last four works is shorter than a total time to perform the first four works and an average time to perform a work for the last four works is generally half of an average time to perform a work for the first four works. Since an accuracy rate for the subject P showed 100%, it can be considered that the subject P carries out the works based on the comprehension on significance (content) of the works.

If we focus attention on a waveform of time change data, increase of the oxyHb amount is found at generally the same time as the timing of completion of each work until the first four works (a peak o1, o2, o3, o4 of an upward convexity). In addition, increase of the deoxyHb amount is found about 5~10 secods behind the timing of completion of each work (a peak d1, d2, d3, d4 of an upward convexity). On the contrary, after completion of the fourth work, in the waveform of the deoxyHb amount, the increase of the deoxyHb amount that has been influenced by the timing of the completion of each work is not found and the deoxyHb amount tends to decrease, and in the waveform of the oxyHb amount, the increase influenced by the timing of completion of each work is not found and the oxyHb amount is constant or tends to increase as a whole so that the two waveforms tend to approach each other.

As mentioned above, since a shape of a waveform of the oxyHb amount and a shape of a waveform of the deoxyHb amount show a distinguished difference between a process until strategy is acquired and a process after the strategy is acquired, there is a strong correlation between the shapes of the waveforms and the timing to acquire strategy and there is a big possibility that timing point when a change of the shape of the waveform of the time change data is found is regarded as timing of strategy acquire.

As mentioned above, in accordance with the device for measuring strategy acquisition 1, it is possible to know timing when the subject P acquires strategy to the work from a characteristic of a waveform of a time change of the oxyHb amount and the deoxyHb amount output by the output portion 4. By making use of the above, it is possible to obtain a tendency or a characteristic in performing a work for the subject P such as "Whether strategy is acquired or not in performing a work?" or "Which is longer a time to take in performing a work before strategy is acquired or a time to take in performing a work after strategy is acquired?" As a result, a tendency or a characteristic of learning for a subject P that the subject P himself or herself has not been aware of becomes clear and then it is possible for a learning instructor to design a pertinent method or curriculum of education set for each subject P.

In addition, since the device 1 uses a near-infrared spectroscopy, it is non-invasive and small in constraining degree for the subject P compared with other measuring device such as an fMRI. In addition, the predetermined measuring region S is set at the frontal lobe that is easy to mount the device 1, which makes it possible to conduct the measurement under a natural environment. Further, since the measuring portion 2 is small with a type of one-channel in this embodiment, unnecessary burden can be avoided for the subject P under a condition of problem solving that is susceptive to an external influence.

In addition to this, since the device 1 is simple in arrangement having one channel and does not require a complicated process such as image processing, the arrangement of the device 1 can be simplified in a cy-pres manner.

The head portion fixing member 5 can appropriately restrain a movement of a head portion that tends to move at a time to solve a problem and then it is possible to conduct an accurate measurement.

A second embodiment of the present claimed invention will be explained with reference to FIG. 6 through FIG. 11.

Second Embodiment

Figure 6:
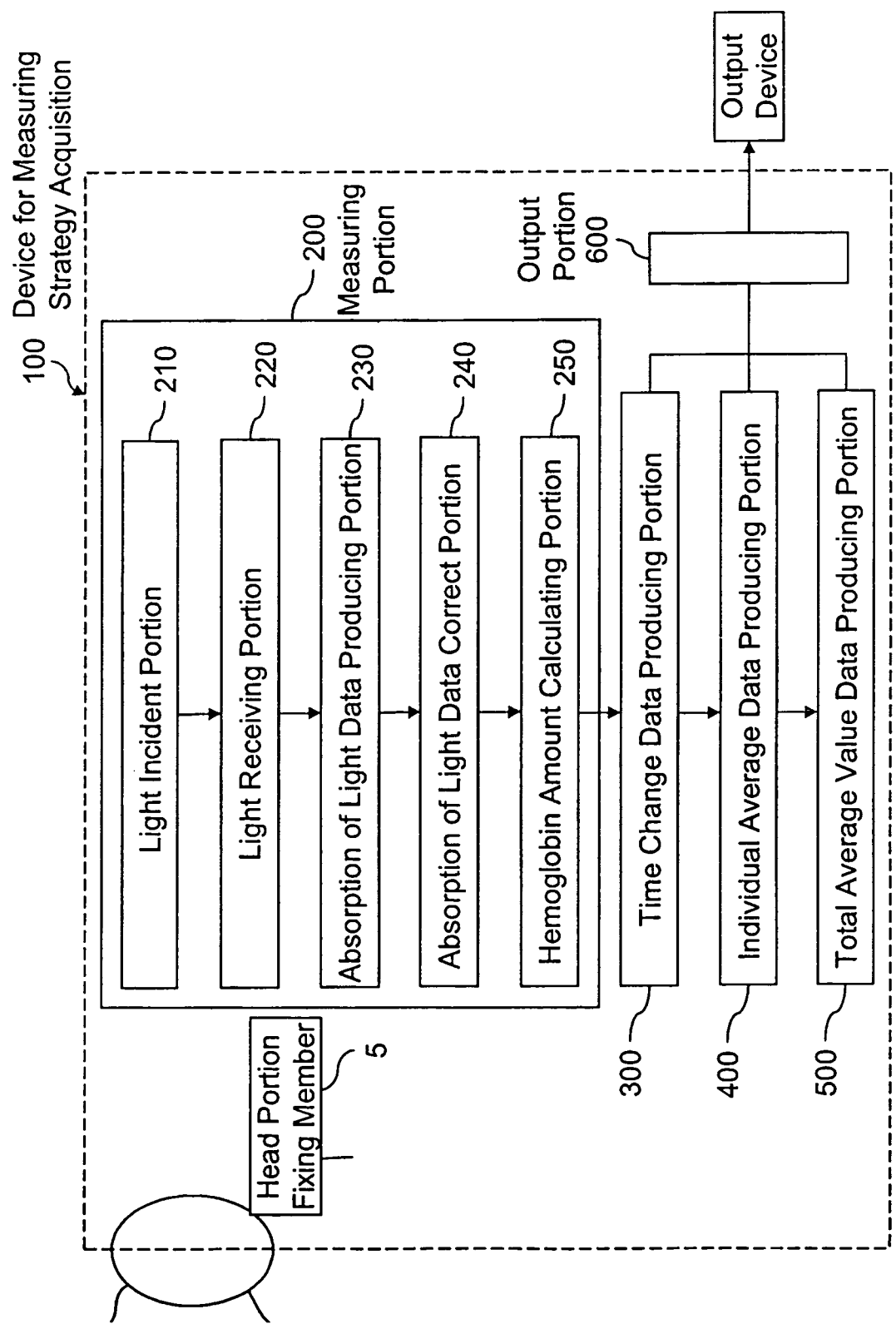
FIG. 6 is a whole functional structural view of the device for measuring strategy acquisition in accordance with another embodiment of the present claimed invention.

A device for measuring strategy acquisition 100 is similar in its configuration to that of the device for measuring strategy acquisition 1 and comprises, as shown in FIG. 6, a measuring portion 200, a time change data producing portion 300, an individual average value data producing portion 400, a total average value data producing portion 500, an output portion 600 and a head portion fixing member 5 as a fixing means. Since the head portion fixing member 5 is equivalent to the head portion fixing member 5 of the first embodiment, an explanation is omitted.

First, in this embodiment, works performed by a subject will be explained. In this second embodiment, two kinds of works K1, K2 are performed by the subject.

A material of the work K1 is similar to that used in the first embodiment and the work K1 is to answer a number of a work graphic form Z2 that is congruent with a designated graphic form Z1 out of multiple work graphic forms Z2 by making use of a transparent auxiliary sheet A. The work K2 is to answer a number of the work graphic form Z2 that is congruent with the designated graphic form Z1 out of multiple work graphic forms Z2 without the transparent auxiliary sheet A.

The subject conducts the work K1 continuously five times and subsequently conducts the work K2 continuously five times. Since the work graphic forms Z2 differ each five times, a number of the work graphic form Z2 that is judged to be congruent with the designated graphic form Z1 differs. In either case of the work K1 and the work K2, the subject takes a rest of 30 sec after completion of each work.

The measuring portion 200 of this embodiment is similar in its fundamental function to that of the measuring portion 2 of the first embodiment and makes use of an NIRS (a near-infrared spectroscopy) wherein near-infrared light of multiple different wave lengths (three wave lengths) radiated from a semiconductor laser or the like is irradiated on the predetermined measuring region S and each of the near-infrared light reflecting off inside the brains is received by a photo acceptance element and measures an oxyHb amount and a deoxyHb amount in blood or tissue by absorption of light of each wave length of near-infrared light that is obtained based on light intensity of the irradiated light and the reflected light and that is a parameter having correlation with the oxyHb amount and the deoxyHb amount. The measuring portion 200 comprises a light incident portion 210, a light receiving portion 220, a absorption of light data producing portion 230, an absorption of light data correct portion 240 and a hemoglobin amount computing portion 250 as a calculating portion. Predetermined parameter data described in claim 12 and having correlation with a blood amount or/and a blood component amount is absorption of light data and parameter data correct portion corresponds to the absorption of light data correct portion 230.

Since each of the light incident portion 210 and the light receiving portion 220 is similar to the light incident portion and the light receiving portion of the first embodiment respectively, an explanation will be omitted.

The absorption of light data producing portion 230 converts the reflected light received by the light receiving portion 220 into an electronic signal, calculates absorption of light by logarithmically calculating the electric signal into a ratio value of a reflected light intensity signal converted into a digital signal by an A/D converter to an irradiated light intensity signal and produces absorption of light data showing the absorption of light at a predetermined timing during conducting a work by storing the ratio value in a predetermined memory portion in association with a corresponding time axis. In addition, since it is difficult to know an absolute value of the irradiated light intensity signal, it is often the case that a constant determined hardwarily or softwarily in the device is practically used instead of the irradiated light intensity signal.

The absorption of light data correct portion 240 is to baseline correct the absorption of light and corrects the absorption of light by making use of difference between the absorption of light data based on the reflected light intensity detected while the subject conducts the works and baseline data. In this embodiment, the baseline data is expressed by a different function for the work K1 and the work K2 respectively. In the absorption of light data producing portion 230, when the absorption of light data is calculated by the use of the constant determined hardwarily or softwarily instead of the absolute value of the irradiated light intensity signal, the value does not have a concrete meaning physically and the value is nothing but a mere logarithmic transformed value of a signal value. However, since the baseline correction is to calculate the difference between the absorption of light data and the baseline data and difference between a logarithmic transformed absorption of light data and a logarithmic transformed baseline data is obtained, the constant can be eliminated. As a result, the difference value physically has a concrete meaning as attenuation of light to the baseline.

More concretely, a time function $F_{base}1(t)$ expressing baseline data during conducting the work K1 is expressed by a constant function wherein a constant is a value of absorption of light data $A1_{start}$ at a start point of time $T1_{start}$ when a first trial of the work K1 is conducted. More specifically, $F_{base}1(t)=A1_{start}$. In addition, a time function $F_{base}2(t)$ expressing baseline data during conducting the work K2 is expressed by a constant function wherein a constant is a value of absorption of light data $A2_{start}$ at a start point of time $T2_{start}$ when a first trial of the work K2 is conducted. More specifically, $F_{base}2(t)=A2_{start}$ (refer to FIG. 8)

The hemoglobin amount computing portion 250 calculates the oxyHb amount and the deoxyHb amount in blood from the absorption of light data at each wavelength baseline-corrected by the absorption of light data correct portion 240 processed by making use of the Modified Lambert-Beer law with the use of a calculating device such as a CPU.

The time change data producing portion 300 chronologically obtains the oxyHb amount and the deoxyHb amount baseline-corrected by the absorption of light data correct portion 240 by sampling them at predetermined intervals, stores each amount in a predetermined memory portion and produces time change data of a hemoglobin amount as data showing time change of a corrected oxyHb amount, a corrected deoxyHb amount and a total hemoglobin amount calculated from the corrected oxyHb and deoxyHb amounts.

The individual average value data producing portion 400 calculates average values of the oxyHb amount, the deoxyHb amount and the total hemoglobin amount from the start point of time to completion point of time of repeatedly conducted each work based on the time change data of the hemoglobin amount, stores the average values in a predetermined memory portion in association with each subject and produces individual average value data of hemoglobin amount showing average values of the oxyHb amount, the deoxyHb amount and the total hemoglobin amount while each individual of subject conducts each work.

The total average value data producing portion 500 calculates an average value of the hemoglobin amount while all of the subjects conduct the works from the individual average value data of the hemoglobin amount for each subject produced by the individual average value data producing portion 400 and produces a hemoglobin amount total average value data showing average values of the oxyHb amount, the deoxyHb amount and the total hemoglobin amount for all subjects for each work.

The output portion 600 outputs a waveform (refer to FIG. 10) of the time change data at least while the subject conducts the work to a display or a printer. In this embodiment, a time change of uncorrected absorption of light data (refer to FIG. 7), baseline data that is applied to correction (refer to FIG. 8), a time change of baseline-corrected absorption of light data (refer to FIG. 9) and total average value data (refer to FIG. 11) of hemoglobin amount produced by the total average value data producing portion 500 are output.

Next, a case that five subjects conduct the above works K1, K2 by the use of the device for measuring strategy acquisition in accordance with this embodiment will be explained.

Figure 7:
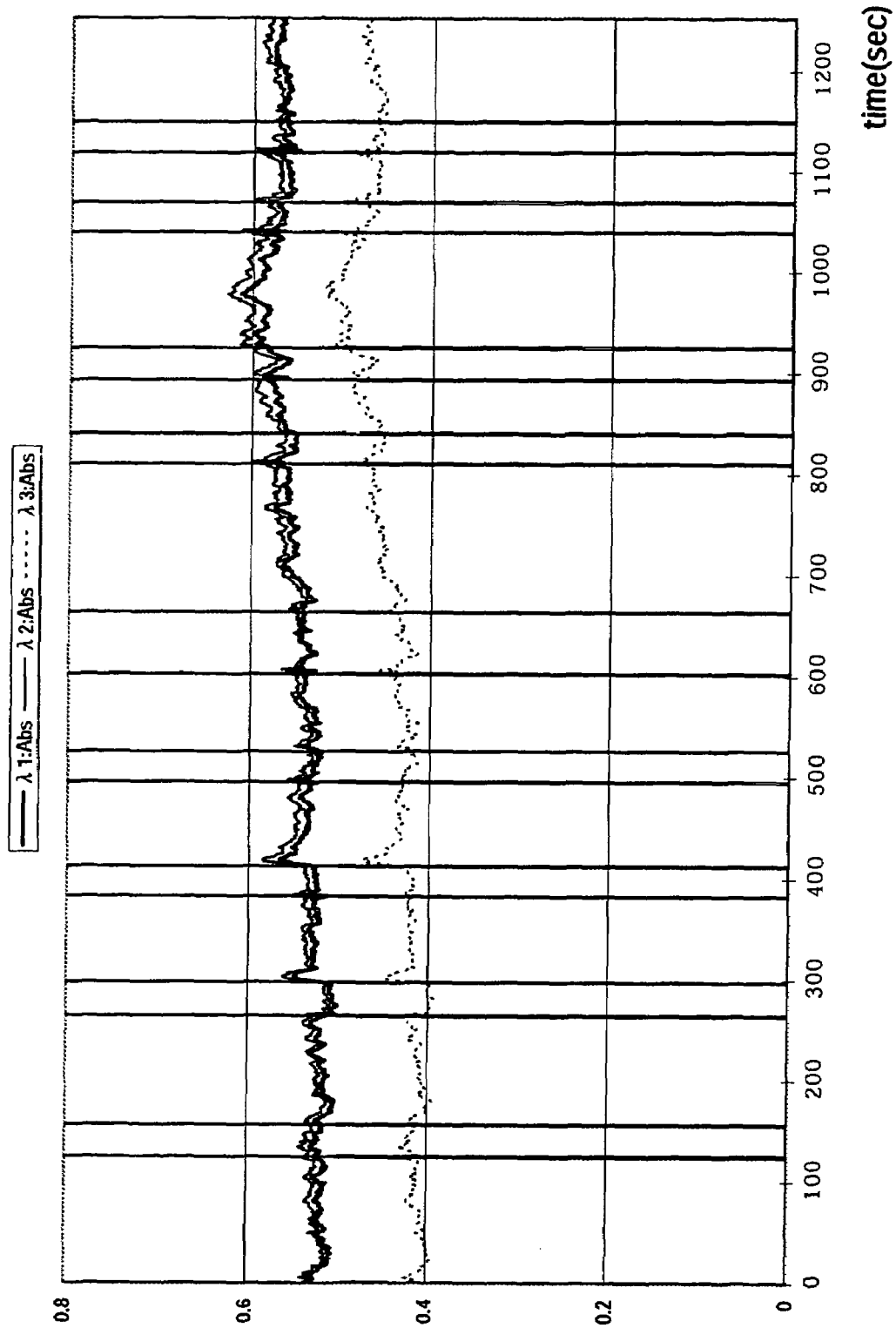
FIG. 7 is a waveform chart showing a waveform of absorption of light data during a process of performing a work in accordance with the embodiment.
Figure 8:
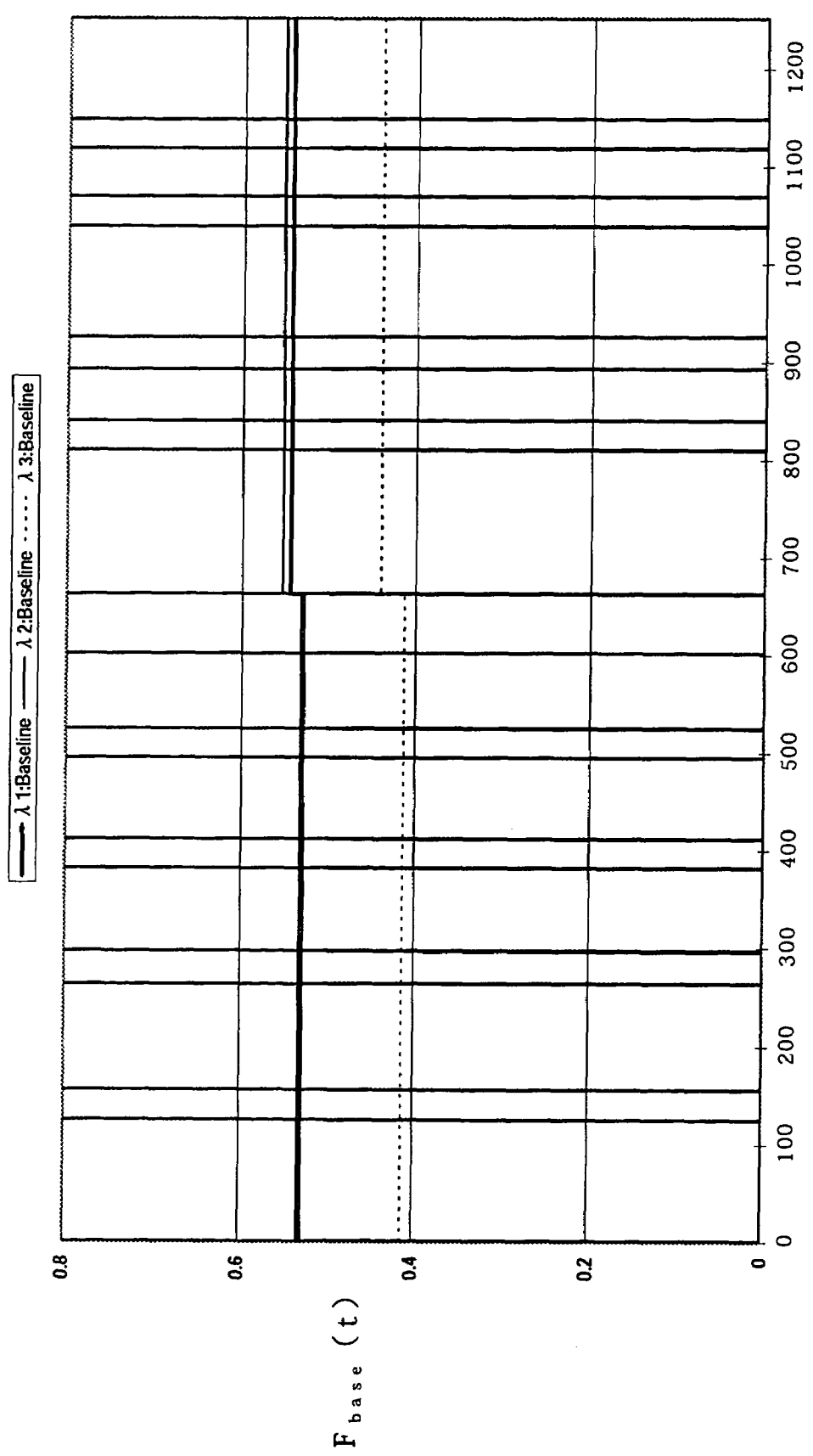
FIG. 8 is a view showing baseline data of absorption of light data in accordance with the embodiment.
Figure 9:
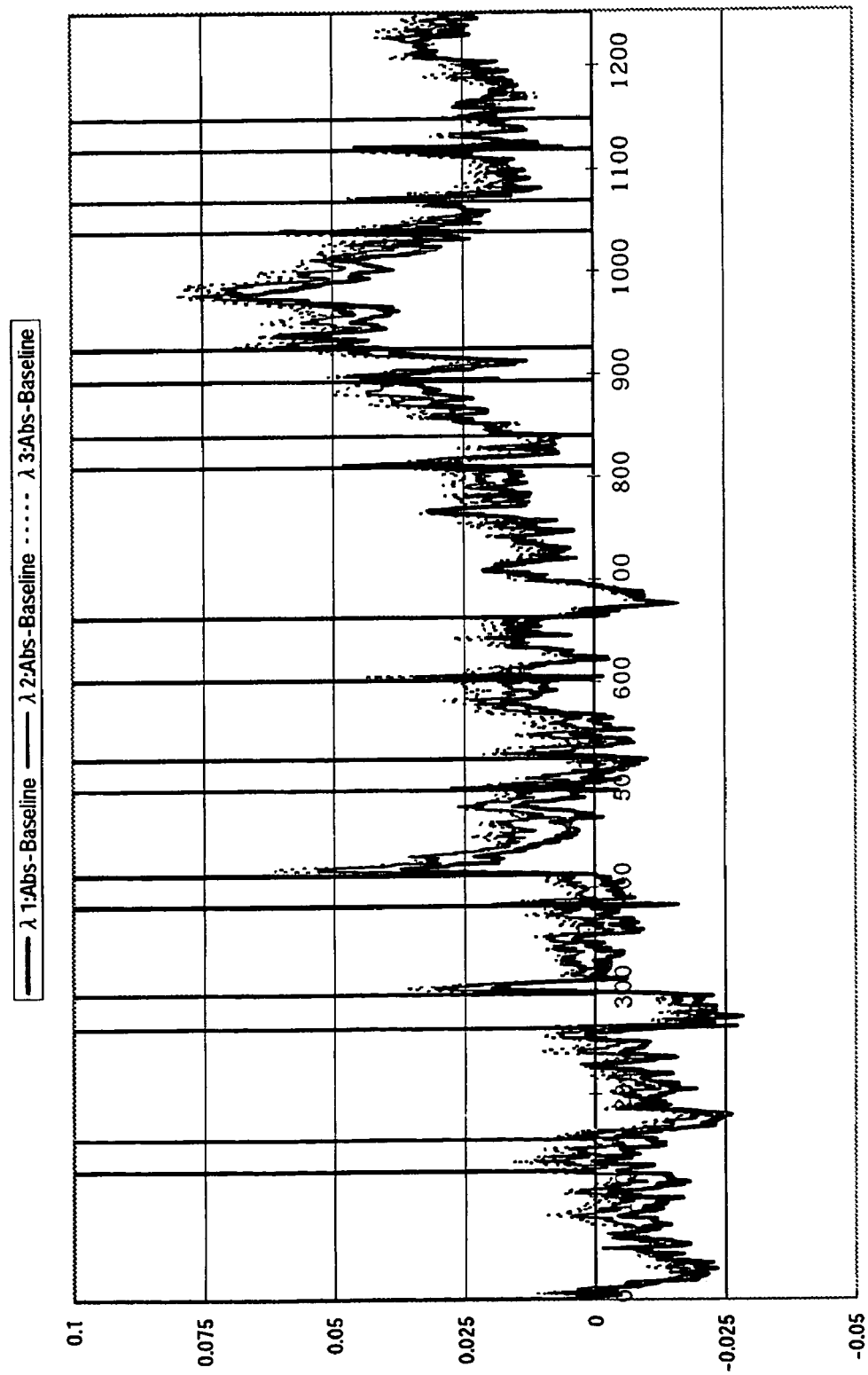
FIG. 9 is a waveform chart showing a waveform of corrected absorption of light data in accordance with the embodiment.
Figure 10:
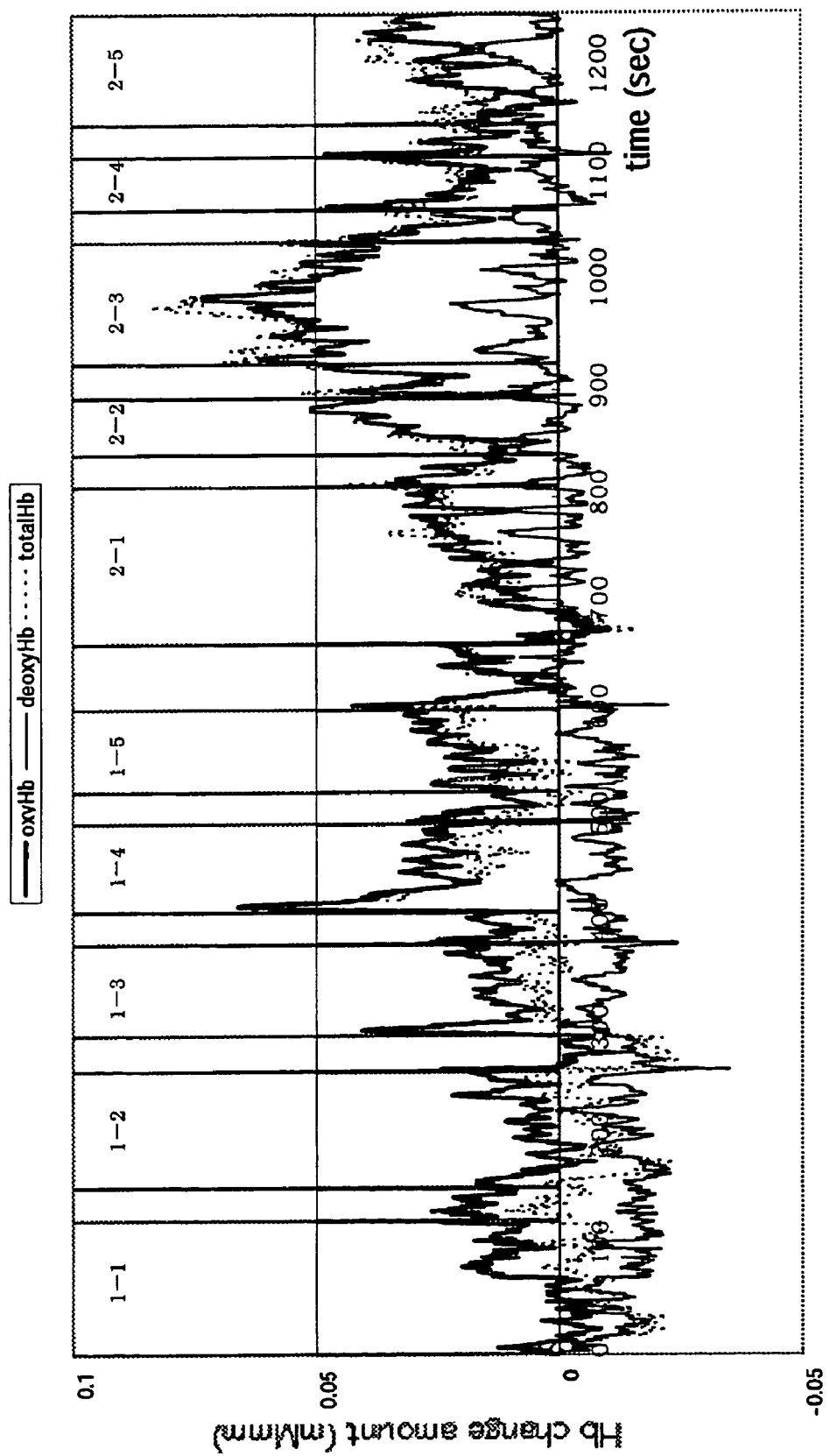
FIG. 10 is a waveform chart showing a waveform of time change data during a process of performing a work based on the corrected absorption of light data in accordance with the embodiment.

Each of FIG. 7 through FIG. 10 shows data of a subject P1 out of the five subjects. More concretely, FIG. 7 shows a time change of raw absorption of light data that is not corrected and that is obtained during conducting the work. FIG. 8 shows baseline data in order to baseline-correct the absorption of light data. FIG. 9 shows baseline-corrected absorption of light data. FIG. 10 shows time change data showing a time change of the oxyHb amount, the deoxyHb amount and the total hemoglobin amount calculated from the baseline-corrected absorption of light data.

Figure 11:
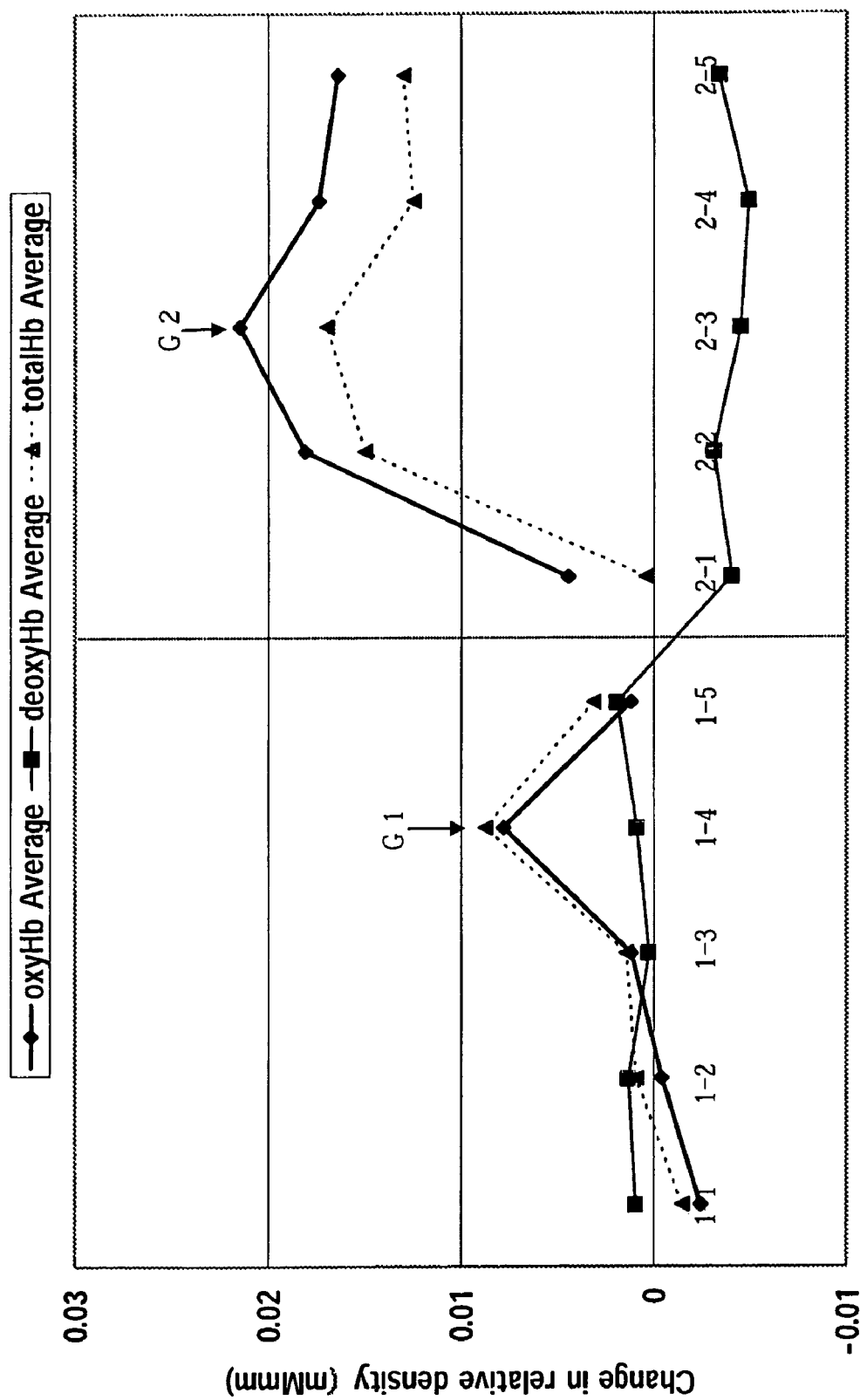
FIG. 11 is a view showing hemoglobin amount total average data in accordance with the embodiment.

FIG. 11 shows total average value data of a hemoglobin amount showing average values of the oxyHb amount, the deoxyHb amount and the total hemoglobin amount for each work for each subject. In FIG. 11, 1-1 through 1-5 are data in conducting the work K1, and 2-1 through 2-5 are data in conducting the work K2.

Timing of strategy acquisition for the subject P1 is detected from the time change data.

Since oxygen is consumed according to activities of nerve cells during a process of conducting works, oxygen by existing oxyHb is supplied to brain and a deoxyHb amount increases. Then it is conceived that an oxyHb amount increases due to arterial blood flowing in the brain in order to supply oxygen continuously according to increase of deoxyHb. In view of a situation that once strategy is acquired, necessity for supplying oxygen to the brain in order to perform the work becomes low, a time point when the oxyHb amount changes from increasing to a constant state or decreasing is considered to be timing of acquiring strategy.

As shown in FIG. 10, in the work K1 shown as 1-1 through 1-5 each waveform of time change data of the oxyHb amount and the total hemoglobin amount shows the maximum at a first half of the fourth trial (1-4) and is kept in a generally constant value during a last half of the forth trial to the fifth trial although it decreases at a time of rest in the forth trial. In the work K2 shown as 2-1 through 2-5 each waveform of time change data of the oxyHb amount and the total hemoglobin amount shows the maximum at the third trial and decreases later.

More specifically, it is judged that a time point when the subject P1 conducts the first half of the forth trial of the work K1 is the timing when the subject P1 acquires strategy for the work K1. In addition, it is judged that a time point when the subject P1 conducts the third trial of the work K2 is the timing when the subject P1 acquires strategy for the work K2.

In addition, in accordance with FIG. 11, each average value of the five subjects of the individual average value of the oxyHb amount and the individual average value of the total hemoglobin amount is the maximum (G1 in FIG. 11) when the five subjects conduct the fourth trial (1-4) in case the work K1 is repeatedly conducted. In case the work K2 is repeatedly conducted, each average value of the five subjects of the individual average value of the oxyHb amount and the individual average value of the total hemoglobin amount is the maximum (G2 in FIG. 11) when the five subjects conduct the third trial (2-3). From these results, "average timing of strategy acquisition" can be considered to be the fourth trial for the work K1 and the third trial for the work K2. This can be supported by impressions of the subjects that the subjects could judge the graphical form to be congruent or not without using the auxiliary sheet A from the forth trial for the work K1 and that the subjects could picture (imagine) the graphical form in mind from the third trial for the work K2.

An average value of five subjects of individual average value of a deoxyHb amount shows no change during a process of conducting the work K1 and the work K2, however, the average value obtained for the work K1 is considerably larger than the average value obtained for the work K2. Further, the average value of the oxyHb amount obtained during conducting the work K2 is considerably larger than that obtained during conducting the work K1. This is considered to be an obvious difference of brain activity resulting from a difficulty level of the work K1 and the work K2.

As mentioned above, in accordance with the device for measuring strategy acquisition 100, it is possible to obtain timing that the subject acquires strategy for a work from a shape of a waveform of the time change data for each subject.

Especially, in this embodiment, since time change data is produced based on the oxyHb amount and the deoxyHb amount baseline-corrected corresponding to two different kinds of the work K1 and the work K2 each of whose difficulty level differs, it is possible to obtain the timing that the subject acquires strategy with high reliability.

In addition, in this embodiment, since the total average value data of the hemoglobin amount is produced and output, it is possible to know an average timing when multiple subjects acquire strategy. More specifically, the device is very useful because it is possible to obtain a standard value of timing to acquire strategy for every work.

The present claimed invention is not limited to the above embodiments.

For example, the output portion may output not a waveform of time change data like the above embodiment but a numeric value of a blood amount or/and a blood component amount measured/calculated by the measuring portion at a predetermined interval. In addition, the output portion may output, for example, data wherein waveforms of time change data is processed with an appropriate calculation such as the Fourier transform or second order derivation.

In addition, in the first embodiment a strategy acquisition calculating portion to calculate timing of strategy acquisition automatically for the subject P based on the time change data may be further provided. Further, in the second embodiment a strategy acquisition calculating portion to calculate timing of strategy acquisition automatically for the subject P based on the total average value data of the hemoglobin amount may be further provided.

In addition, a text material for the work may be further added to a component element of the device.

It is a matter of course that the work is not limited to the work in the above embodiments, a number or a content of the work may be changed. In addition, in the first embodiment, an experimental result is obtained by judging whether the graphical form is congruent or not, so to speak "object operation", by making use of the auxiliary sheet A, however, an experiment of "thinking operation" wherein no tool such as an auxiliary sheet is used may be conducted and these operations may be compared in a situation of strategy acquisition. In accordance with the experiment, there is a possibility to obtain data that can be an index to development of a new educational practice in graphical education.

In addition, a means to measure timing of completion of the work automatically may be further provided.

In addition, the device itself may comprise an output device such as a printer or a display.

Further, it is a matter of course that the fixing means is not limited to the fixing means of the above embodiment as long as it can restrain a movement of a head portion without interfering a movement of performing works for a subject. For example, the fixing means may be integrated into a desk or may be supported by a ceiling of a laboratory where the experiment is conducted.

Other concrete arrangement is not limited to the above-described embodiment and may be variously modified without departing from the spirit of the invention.

What is claimed is:

1. A device for measuring strategy acquisition when a subject performs a predetermined assignment of work comprising:
   a measuring portion that measures an oxyHb amount in blood in a predetermined measuring region of a brain of a subject;
   a time change data producing portion that obtains the oxyHb amount in the blood measured by the above-mentioned measuring portion chronologically and that produces time change data as data showing time change of the oxyHb amount in the blood;
   an average data producing portion that calculates average values of the oxyHb amount, from the start point of time to the completion point of time of conducting each work, and produces average value data indicating an average value of the oxyHb amount while the subject conducts each assigned work based on the time change data produced by the time change data producing portion in case the subject conducts multiple works that can be solved using a definite law or regularity; and
   an output portion that displays or outputs the average value data produced by the average value data producing portion.

2. The device for measuring strategy acquisition according to claim 1 wherein the measuring portion measures an amount deoxyHb in the blood.

3. The device for measuring strategy acquisition according to claim 1 wherein the predetermined measuring region is an area corresponding to a higher brain function portion of the subject.

4. The device for measuring strategy acquisition according to claim 1 wherein the predetermined measuring region is set at a frontal lobe of the subject.

5. The device for measuring strategy acquisition according to claim 1 wherein the measuring portion measures the oxyHb amount in the blood by making use of a near-infrared spectroscopy.

6. The device for measuring strategy acquisition according to claim 5 wherein the measuring portion is of one channel.

7. The device for measuring strategy acquisition according to claim 1 further comprising a fixing means to a head portion of the subject.

8. The device for measuring strategy acquisition according to claim 1 wherein
   the measuring portion can calculate the oxyHb amount in the blood that is baseline-corrected corresponding to the work conducted by the subject, and
   the time change data producing portion is made to obtain the baseline-corrected oxyHb amount in the blood chronologically and to produce the time change data.

9. The device for measuring strategy acquisition according to claim 8 wherein the measuring portion calculates a measured value of the oxyHb amount in the blood based on a predetermined parameter data that is correlative to the oxyHb amount in blood.

and further comprising a parameter data correct portion that baseline-corrects the above-described parameter corresponding to the work and a computing portion that calculates the oxyHb amount in the blood by the use of the parameter data corrected by the parameter data correct portion.

10. The device for measuring strategy acquisition according to claim 9 wherein the parameter data correct portion is to correct the parameter data with a difference value between the parameter data obtained while the subject conducts the work and baseline data expressing a baseline, and the baseline data is expressed by a function that varies corresponding to a content of the work.

11. A method for measuring strategy acquisition, in case a subject conducts multiple works that can be solved using a definite law or regularity comprising:

determining an oxyHb amount in the blood in a predetermined measuring region of a brain of the subject that is measured chronologically by the use of near-infrared spectroscopy;

calculating average values of the oxyHb amount corresponding with each work based on the time change data as data showing the time change and determining average value data indicating an average value of the oxyHb amount on each work;

producing an average value data showing the average value of the oxyHb amount during the time period the subject conducts each work, and displaying or printing the average value data, wherein a state of strategy acquisition to solve the work for the subject is determined.

12. A device for measuring strategy acquisition of a work project, comprising:

a measuring unit that measures an oxyHb amount in blood at a predetermined measuring region in a person's brain where strategy acquisition of the work project occurs;

a time change data producing unit that receives the oxyHb amount in blood measured by the measuring unit and generates time change data corresponding to time change of the oxyHb amount in blood;

an average data producing unit that averages the oxyHb amount in blood measured for the work project that the person conducts, from the start point of time to the completion point of time of conducting each work, based on the time change data produced by the time change data producing unit when the person performs the work project that can be solved using a definite law or regularity, and generates average value data for the work project; and an output unit that outputs the average value data produced by the average value data producing portion.

13. A method for measuring strategy acquisition of a work project that can be solved using a definite law or regularity, the method comprising the steps of:

measuring chronologically an oxyHb amount in blood at a predetermined measuring region in a person's brain where strategy acquisition of the work project occurs;

generating time change data corresponding to the time change of the oxyHb amount in blood;

generating average value data corresponding to the average value of the oxyHb amount in blood measured for the work project based on time change data; and outputting the average value data to determine the state of strategy acquisition for solving the work project.

* * * * *